United States Patent [19]

Irnich

[11] Patent Number: 4,516,579
[45] Date of Patent: May 14, 1985

[54] INTERFERENCE RECOGNITION CIRCUIT IN A HEART PACEMAKER

[76] Inventor: Werner Irnich, 3 Birkenweg 60, D-6301 Wettenberg, Fed. Rep. of Germany

[21] Appl. No.: 527,177

[22] Filed: Aug. 26, 1983

[30] Foreign Application Priority Data

Sep. 1, 1982 [DE] Fed. Rep. of Germany ....... 3232478

[51] Int. Cl.³ .............................................. A61N 1/00
[52] U.S. Cl. ............................................. 128/419 PG
[58] Field of Search ................. 128/419 PG, 696–698, 128/708

[56] References Cited

U.S. PATENT DOCUMENTS

| | | | |
|---|---|---|---|
| 3,811,428 | 5/1974 | Van Horn et al. ................... | 128/698 |
| 3,881,493 | 5/1975 | Cannon .......................... | 128/419 PG |
| 3,905,364 | 9/1975 | Cudahy et al. ....................... | 128/696 |
| 3,927,677 | 12/1975 | Gobeli et al. ................. | 128/419 PG |
| 3,985,142 | 10/1976 | Wickam ....................... | 128/419 PG |
| 4,478,224 | 10/1984 | Bailey ..................... | 128/708 |

Primary Examiner—William E. Kamm
Assistant Examiner—Mitchell J. Shein
Attorney, Agent, or Firm—Ernest F. Marmorek

[57] ABSTRACT

A synchronizable heart pacemaker includes a timing circuit, a differentiating circuit for receiving signals, and an interference recognition circuit connected to the output of the differentiating circuit. The interference recognition circuit includes a testing stage for each signal. An output signal normally appears on an output of the testing stage, and the testing stage includes a peak detector circuit which stores a positive maximum value and a negative maximum value of each signal differentiated by the differentiating stage, and an adder forming the sum of said maximum values. A discriminator stage is postcoupled to the testing stage. The discriminator stage generates a time interval corresponding approximately to a time duration of the QRS-complex of a heart-action signal, and includes a checking circuit for checking the presence or absence of the output signal of the testing stage after said time interval, and a decision circuit for recognizing the output signal either as an interfering signal, and thereafter rendering the interfering signal ineffective, or recognizing the output signal as the heart-action signal, and passing the heart-action signal to the timing circuit.

20 Claims, 9 Drawing Figures

Fig. 1: Blockdiagram (1) = Differentiator
(2) = Preamplifier
(3) = Peak detector
(4) = Signal conditioner
(5) = Delay
(6) = Refractory
(7) = Coincidence

$f_g$ = 1 KHz
$R_1$ = 100 KΩ
$C_1$ = 1.5 nF

Fig. 4:

OP1 = 8021
$R_2$ = 22 KΩ
$R_3$ = 1 KΩ
$C_2$ = 5 nF
$f_g$ = 1.5 KHz

50Hz-suppression: $(1 - e^{-10ms/3s}) = 3.3 \cdot 10^{-3}$

Fig. 6:

$R_8 = R_9 = R_{10} = 470K\Omega$, $R_{11} = R_{13} = 3.3M\Omega$, $R_{12} = 100K\Omega$,
$R_{14} = 2.2M\Omega$, $R_{15} = 470K\Omega$, $R_{16} = R_{17} = 1M\Omega$, $C_5 = 33pF$
OP2 = 8021, OP3 = 8021

MF2 = CD 4047
$R_{19}C_7 = 250 \div 300$ ms
$C_8 = C_9 = 1$nF
$R_{20} = R_{21} = 1$MΩ
$R_{22} = 2.2$MΩ
NOR1 = CD 4572
$D_3 = D_4 = $ 1N4148

J = "1" : Interference !

Truth table:

| E | G | $\bar{E}$ | $\bar{G}$ | H | |
|---|---|---|---|---|---|
| 0 | 0 | 1 | 1 | 0 | |
| 1 | 0 | 0 | 1 | 0 | |
| 0 | 1 | 1 | 0 | 0 | |
| 1 | 1 | 0 | 0 | 1 | Heart signal ! |

INTERFERENCE RECOGNITION CIRCUIT IN A HEART PACEMAKER

BACKGROUND OF THE INVENTION

The invention relates to a synchronizable heart pacemaker having a timing circuit and an interference recognition circuit, which includes a testing stage for each signal, and a discriminator stage postcoupled to the testing stage, in which the presence or absence within a predetermined time interval of an output signal from the testing stage is determined. The predetermined time interval corresponds approximately to the QRS complex of a heart-action signal. As a result of this test the signal is either recognized as an interfering signal, and rendered ineffective, or is recognized as a heart-action signal, and fed to the timing circuit.

Pacemakers including interference recognition circuits of this kind operate according to the "principle of time analysis". In this principle of time analysis one starts from the fact that a heart-action signal has a characteristic form, which is characterized by a spike-like initial portion and a waveform following thereafter which is broader in shape than the spike-like initial portion, and wherein normally no further heart-action signal appears within a time interval from 180 to 200 ms following commencement of the heart-action signal. The principle of time analysis is therefore based on a test whether any further signal appears within the approximate duration of the Q-T-complex of the heart-action signal (refraction time or refractory period). If this is the case, then any further signal present is evaluated as an interfering signal.

In general current pacemakers, almost without exception, are in a position to take actions of the heart into account in a suitable manner. For example, one version of a pacemaker is programmed to discontinue operations, if the heart has a sufficiently high frequency, or rate of beats of its own (Demand pacemaker). Another version of a pacemaker attempts to implement or simulate the action of the auricle, and to generate therefrom a stimulation impulse for the ventricle, so as to ensure synchronization between the auricle and the chamber (auricle-controlled ventricular pacemaker). In spite of the physiological advantages systems of this type have to contend with the problem that any interfering signals could upset the circuit. Here it is necessary to differentiate between exogene and endogene interference sources. Exogene interference sources are due to magnetic, electrical, as well as electromagnetic fields, or are simply due to galvanic contacts of parts carrying any voltage. Endogene interferences are generated when any muscle signals, or the T-wave of the electrocardiogram, or, in the case of auricle electrodes, the R-wave of the ventricle are encountered in the auricle.

All interference-recognition circuits attempt to find differences between the enumerated sources of interference and the actual synchronizing heart signals, which are then required to be discriminated by electronic means. This is accomplished in practically all pacemakers now on the market by an active or a passive bandpass filter, which has a lower pass-frequency lying between 5 Hz and 20 Hz, and an upper pass-frequency lying between 50 Hz and 100 Hz. It has been shown, however, that a mere filtering of frequencies is not in a position to differentiate adequately between interfering signals, and operative signals, also primarily due to the fact that the most frequent interference is that of the mains supply (In Europe 50 Hz, and in the U.S. 60 Hz), which can almost certainly not be suppressed.

More effective discriminating methods can only be expected if the typical structure of an intracardiac signal, irrespective whether it is atrial or ventricular, is taken into account. A description of typical waveforms is given below, which applies when the heart signal is obtained in a unipolar manner (one electrode is disposed very close to the heart wall, the other electrode is very remote therefrom). In this case a very typical signal is registered, which starts with a more-or-less large positive peak, changes shortly thereafter to a negative peak, and wherein a positive peak of reduced steepness follows. A subsequent broader waveform, namely a waveform having a predominantly low-frequency content compared to that of the peaks, may have different shapes; for example, its positive portion can be relatively large, particularly in case of any first implantation, but this portion can also be missing altogether, particularly in the case of electrodes which have been implanted for some time. In each case there arises towards the end of the heart action again a somewhat broader negative wave, denoted as a T-wave. It has been found that, as an average, the fall time of the initial negative peak amounted to 4.6 ms (region between 0.5 and 10.9 ms), while the subsequent rise time amounted to, as an average 17.3 ms (region between 6.8 and 35 ms), so that the ratio between the fall time and the rise time is about 1:4. To this difference between the fall time and the rise time corresponds a difference between the steepness of flanks or trails of the negative-going and the positive-going signals, which difference has a ratio of 4:1. This typical structure can be explained theoretically in a manner such that a wave having the character of a dipole passes immediately along the electrode, whose positive charge initially results in a positive signal, but which, upon the positive charge moving immediately below the electrode, is quickly reshaped, so as to assume the negative extreme value when passing the negative charge. The further progress or shape of the wave is then determined by the far field of this dipole wave. Signals of the remote field do not have comparable steepnesses, so that examination relating to steepness of the flanks or trails permits the achievement of an effective discrimination between signals in the remote field (excitation of the respective other chamber, or muscle signals) and those of the near field.

In a known heart pacemaker circuit of this kind (U.S. Pat. No. 3,985,142), a test stage of the interference recognition circuit consists of a comparator circuit in which the input signal is compared to a reference signal, and wherein the output signal of the comparator circuit is dependent on the result of this comparison.

In this circuit each incoming signal, regardless whether it is an interfering signal, or an operative signal, starts an expecting interval. Following a short refraction time, a test is performed during a relatively short interval, whether a further signal is present or not. In the event such a signal is present, it is evaluated as an interference signal, and an impulse is transmitted at the end of the expecting interval, independent of the fact what type of signal has been obtained from the heart.

It is an advantage of this circuit that each continuous, but also each pulse interference which lasts beyond the refraction time, is recognized by the circuit as an interference, and does not permit the pacemaker to stop operation in such cases.

It is a disadvantage, however, that each commencement of an interference is evaluated as a heart action, and that the circuit is overpowered, if the interference lasts for a time shorter than the built-in refraction time. Any non-recurring signals cannot be recognized as interfering signals.

In summary then, this known interference recognition circuit recognizes continuous and pulsed interfering signals, if these signals continue beyond the predetermined time interval. But it is not in a position to recognize any symmetrical interfering signals as such, if these correspond in their time duration to the heart-action signals, or are shorter than the refraction time.

Another known interference recognition circuit operates according to the "principle of the maximum searcher" (U.S. Pat. No. 3,927,677). In this known circuit for guarding against any interference, a voltage is generated according to the rise of the signal at the input of the amplifier, which includes a peak value storage stage for this purpose. The maximum value is maintained in a capacitor, which is discharged at a certain time constant. Each incoming interfering signal causes such a charging process, and each further interfering signal results in the stored value of the maximum searcher not being changed.

Only when a change of amplitude occurs, such as is the case, for example, when the heart signal is superimposed on an interfering signal, is a signal generated at the output of the peak value storage stage, which only triggers a subsequent timing circuit, when the amplitude exceeds a certain value.

It is an advantage of this circuit that heart signals can be recognized as such, even in the presence of any massive continuous interference.

But it is a disadvantage of a heart pacemaker which includes this interference recognition circuit, that it is not in a position to recognize all amplitude-modulated interference signals as such. An amplitude-modulated interfering signal, which generates at the output of the maximum searcher an adequately large signal, is rather evaluated in this circuit as a heart action signal, and consequently silences the pacemaker.

Experiments conducted by applicant have shown that in the case of an interference which has an amplitude of 100 mV, a rectangular amplitude-modulation of 1.5 mV is in a position to inhibit the pacemaker. As continuous interferences, in practice, are, in fact, a rare exception, this interference recognition circuit basically endangers patients, which necessarily have to rely on this pacemaker. For this reason the manufacturer of this pacemaker has drawn the appropriate conclusions and has no longer utilized the pacemaker in the aforedescribed manner since the end of 1979.

Reference should also be had to applicant's publication "Stoerbeeinflussung von Herzschrittmachern" (Impairment of heart-pacemakers by Interference), Herzschrittmacher 2, 1982, EBM GmbH.

SUMMARY OF THE INVENTION

Starting from the initally described heart pacemaker, it is an object of the present invention to improve the interference recognition circuit in such a pacemaker to such an extent, that any additional symmetrical interference signals, which otherwise correspond in their duration to the heart-action signals, or are shorter than the Q-T-complex of a heart-action signal (refraction time), are recognized as such, and rendered harmless.

This object is attained, according to the invention, by there being provided a differentiating circuit at the input of the heart pacemaker, which consists of a capacitor and a resistor connected with one end thereof in series with the capacitor, and connected with the other end thereof to ground, and by the testing stage consisting of an adder, in which the positive and negative maximum value of each differentiated signal is stored, and wherein a sum is formed from the positive and negative maximum values.

The inventive heart pacemaker circuit represents in a certain sense a combination of the principle of time analysis with the principle of the maximum searcher, by additionally evaluating also the negative maximum value of the differentiated signal. Consequently the circuit responds only to non-symmetrical signals, and is insensitive towards any symmetrical signals, any signals having symmetrical steepness, and any signals wherein the difference in steepness is not sufficiently large, as is the case, for example, in heart signals of the remote field.

BRIEF DESCRIPTION OF THE DRAWINGS

For a fuller understanding of the nature and objects of the invention, reference should be had to the following description, taken in connection with the accompanying FIGS. of the drawing, which further illustrates the construction and operation of the heart pacemaker, and in which:

FIG. 3 through FIG. 9 are details of a more sophisticated implementation of the block diagram according to FIG. 1, in which:

DESCRIPTION OF THE PREFERRED EMBODIMENT

Figure 1:
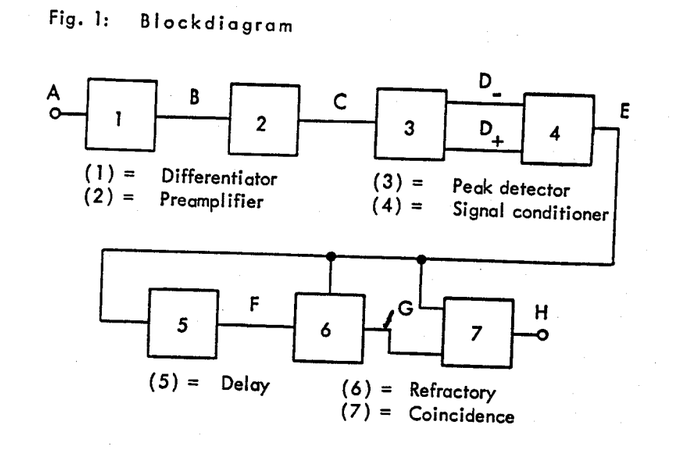
FIG. 1 is a block diagram of the interference recognition circuit, according to the present invention.

Referring now to the drawings, and particularly to FIG. 1, which is block schematic of the circuit, according to the present invention, in order to electronically utilize the characteristic differences in steepness, there are employed differentiating means (differentiator 1), which transform the negative steepness of any signal into a negative voltage, and the positive steepness of any signal into a positive voltage. The output voltage of the differentiating means or stage 1 obtained at the terminal B thereof is passed to a preamplifier 2, and there appears at its output C a voltage amplitude, which can be further processed. The output C of the preamplifier 2 is passed to peak-value storage means, such as peak detector 3, which stores a peak value corresponding both to the negative, as well as to the positive maximum steepness of the signal A; the corresponding output signals $D_-$ and $D_+$ of the storage stage 3 are available for an adequately long time duration. The circuits which follow the storage stage 3 include heart-action signal recognition circuitry, such as interference recognition means for recognizing any non-recurring signal having a predominantly positive rise time, and any periodic pulsed or amplitudemodulated signals as interference signals, and interference suppression means for preventing the interfering signals from being further processed.

In the circuit 4, which is a signal conditioner, discriminator, or testing stage, three tasks are undertaken, so as to obtain at its output E a signal, which is an operative signal. The difference between the negative and positive maximum steepnesses is determined by steepness difference recognition means, such as an adder, which also acts as polarity sensing means, and which further amplifies this difference. If the output signal of this amplifying adder is equal to, or larger than a reference signal, then a comparator is switched at the output E from a low value to a high value ( Transition from analog signal processing to digital techniques). The output signal E of the circuit 4 is passed to a delay circuit 5, which, following a delay time which corresponds approximately to the duration of a QRS complex, switches its output F from a low level to a high level.

In the refractory circuit 6 a delay member is activated by the high level output F during a certain time duration lasting between 200 ms to 300 ms, whose output G is passed to one of the inputs of a coincidence circuit 7. If both inputs of the coincidence circuit 7 receive E and G signals of a high level, a signal having a high level appears at its output H, characteristic a heart-action signal.

The processing of any symmetrical interference signals, or signals having symmetrical steepness of flanks, (for example voltages obtained from dual-path rectifiers) by this circuit proves its effectiveness, and consequently delineates also the principal difference between this circuit and that of all other interference-recognition circuits of the prior art. The differentiating stage transforms the aforesaid signals into other signals having a substantially symmetrical structure. Following amplification in the preamplifier 2, voltages of the extreme values, which are proportional to the steepness of corresponding flanks, are stored in the peak-value storage stage 3; based on the assumption of symmetrical steepness, the addition of these extreme or peak values will, to all intents and purposes, result in a zero sum voltage. These interfering signals will reach, or remain on the level E for only a short time, this level being necessary to activate the circuits which follow.

A "one" will therefore not appear simultaneously with the signal G of the refractory circuit 6 on both inputs of the coincidence circuit 7, so that any interfering signal of the aforedescribed kind will be rejected by the circuit 7. As heart signals of the other chamber, as well as muscle signals are much more symmetrical in their steepness, these signals will also be suppressed at a suitable adjustment of the amplifier, namely if they fall below a predetermined value.

Figure 2:
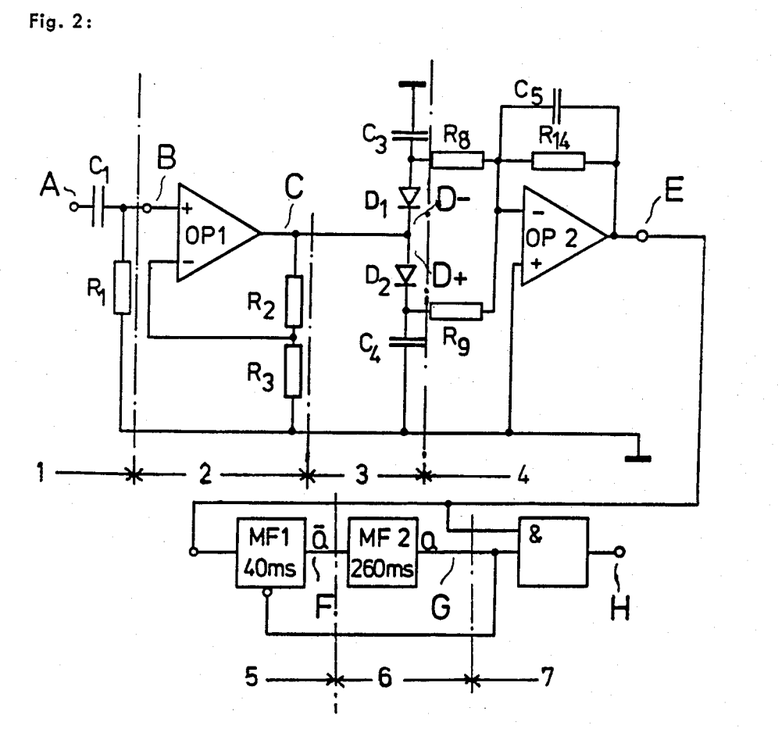
FIG. 2 is a simple implementation of the block diagram, according to FIG. 1.
Figure 3:
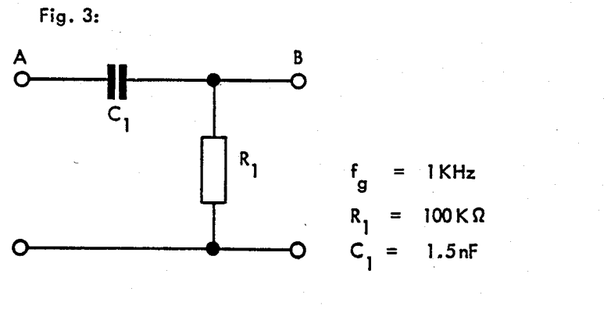
FIG. 3 is a detail of the differentiator.

The block diagram of FIG. 1 can be implemented in its simplest form by the circuit according to FIG. 2. A signal appearing at the input A is differentiated in the differentiating stage consisting of a capacitor $C_1$ and a resistor $R_1$, and its output B is fed to the positive input of the differential amplifier OP1. The ratio of the feedback resistors $R_2/R_3$, fed back to the negative input of the differential amplifier OP1 results in an amplification of the differentiated input signal in such a manner that the steepness signal reaches a level of about 0.5 V to 1.0 V. Capacitors $C_3$ and $C_4$ are charged by respective diodes $D_1$ and $D_2$, the steepness maximum, denoted by $D_+$ appearing on $C_4$, while the steepness minimum, denoted by $D_-$ appears on $C_3$.

The operational amplifier OP2, together with resistors $R_8$, $R_9$ and the resistor $R_{14}$ in the feedback path constitute an amplifying adder, which reproduces on its output E the difference between the steepness maximum and the steepness minimum. In this manner, apart from a short-duration initial signal, the sum signal at the output E of the amplifier OP2 will be zero for any symmetrical interference signal, or an interference signal having symmetrical flanks or trails. The capacitors $C_3$ and $C_4$ are simultaneously slowly discharged through respective resistors $R_8$ and $R_9$ according to their time constants, so that in the case of signals appearing at the rhythm of the heart, the capacitors acting as storage devices are to all intents and purposes always discharged. In this manner the steepnesses of the flanks of each heart signal are stored, and a comparison of the steepness is made. In the case of signals rapidly succeeding each other, which are typical of 50 Hz or 60 Hz interfering signals, insufficient time is available for either capacitor $C_3$ or $C_4$ to be discharged. In this situation the maximum value of steepness is always stored.

The signal at the output E is now tested in a discriminator stage (circuits 5, 6, and 7) whether it is a signal having asymmetrical steepnesses or not. For this purpose each signal appearing at the output E is fed to a monostable multivibrator $MF_1$ having a delay of about 40 ms. The inverted output $\overline{Q}$ of this multivibrator $MF_1$ is fed to the dynamic input of a second monostable multivibrator $MF_2$, which has a time delay of 260 ms. If its output Q is increased from "0" to "1", then a "one" signal will appear across the output of the following AND gate (coincidence circuit 7) if the output signal E of the operational amplifier OP2 has remained positive up to the end of the delay time of the multivibrator $MF_1$. Such a state is only possible if a signal appears at the input A of the entire circuit whose absolute value of negative steepness is clearly larger than that of its positive steepness, which very fact is typical for intracardiac signal. On the other hand each non-reccurring signal having a predominantly positive steepness, and furthermore each pulsed or amplitude-modulated signal will always lead at the output E of the operational amplifier OP2 to a signal which is shorter than the time of the monostable multivibrator $MF_1$, due to the addition of the maximum and of the minimum of the steepnesses.

The signal appearing at the output H, which is only generated if a signal, such as an intracardiac heart signal includes the corresponding steepness criteria, controls a conventional timing circuit, in which, based on the aforesaid signal, either the expectation interval of a demand heart pacemaker is newly started, or a delay circuit is activated according to the AV-conduction time, such as in the case of an auricle-controlled heart pacemaker.

In summary then, the aforesaid circuits include decision means for checking the presence or absence of an output signal E from the signal conditioner stage within a given time interval, and heart-action signal recognition means for recognizing the input signal A either as an interfering signal, and thereafter rendering the interfering signal ineffective, or recognizing the input signal A as the heart action signal, and passing the heart action signal to a timing circuit in the event of the presence of the output signal H after said time interval.

A more sophisticated implementation of the block diagram shown in FIG. 1 are shown individually in FIGS. 3 through 9; here any additional or explanatory features are further discussed. The differentiator 1 shown in FIG. 3 consists of an RC circuit whose constants have been chosen, so that a fall time of 0.5 ms is still differentiated in a somewhat undampened manner. According to the Kuepfmueller formula an upper frequency limit $f_g$ of 1 KHz corresponds to a rise time of 0.5 ms.

Figure 4:
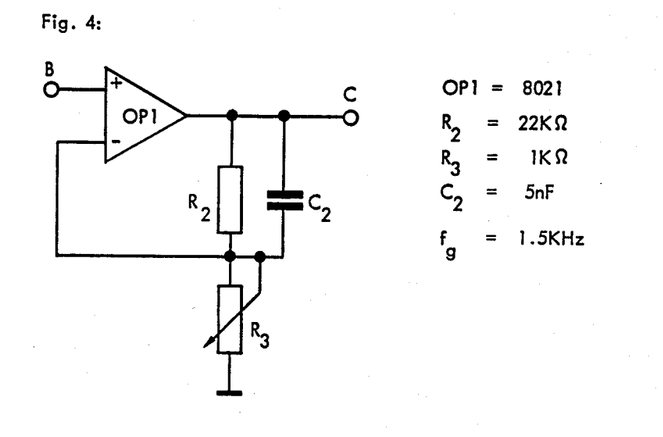
FIG. 4 is a detail of the preamplifier.

The preamplifier 2 shown in FIG. 4 includes a potentiometer $R_3$, so as to render the amplification variable; furthermore, by means of the feedback capacitor $C_2$ the amplification is rendered frequency-dependent. If the upper frequency limit $f_g$ of this low-pass filter is assumed to be 1.5 KHz, then the time constant of the circuit consisting of the resistor $R_2$ and the capacitor $C_2$ has a value of 0.1 ms.

Figure 5:
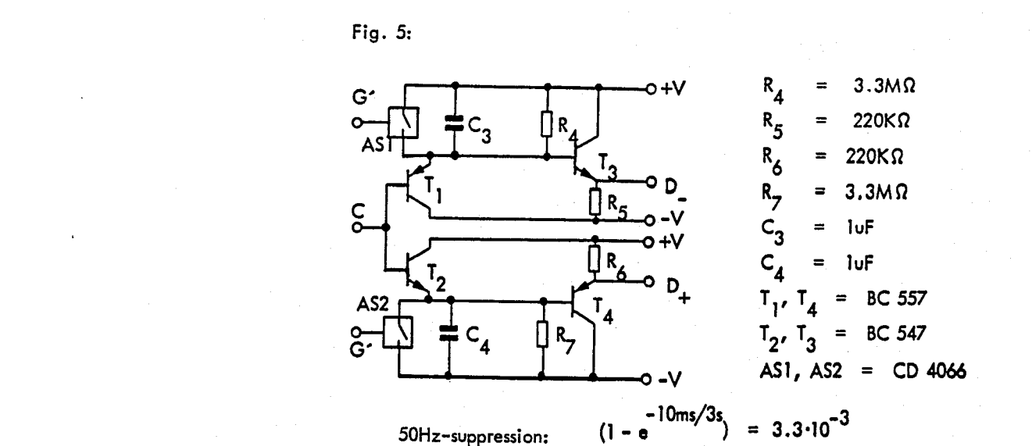
FIG. 5 is a detail of the peak-value storage circuit.

FIG. 5 shows an implementation of the peak-value storage device or peak detector 3, which implementation was found to be optimal for the tasks demanded from it. Instead of the diodes $D_1$ and $D_2$ shown in FIG. 2, the base-emitter diodes of transistors in npn and pnp configurations are coupled to the output C of the preamplifier 2. By this means the output of the preamplifier 2 is effectively not loaded, as seen by its output current, and the transisistors act as emitter-followers. In order to render the capacitors $C_3$ and $C_4$ load-independent of the stage 4 following it, an additional pair of transistors $T_3$ and $T_4$ acting as emitter followers are connected to the capacitors $C_3$ and $C_4$, respectively, however at a polarity opposite to the pair of the preceding transistors.

Not only is decoupling achieved by this means, but also potentials $D_+$ and $D_-$ are created, which are identical with the respective maximum and minimum at the output of the preamplifier 2 (reciprocal compensation of the threshold voltages). The capacitors $C_3$ and $C_4$ are discharged slowly at a time constant of 3 secs through respective resistors $R_4$ and $R_7$. But they can alternately also be discharged quickly through respective analog switches AS1 and AS2, according to the control signal G', which is obtained from the refractory circuit 6 according to FIG. 8.

Figure 6:
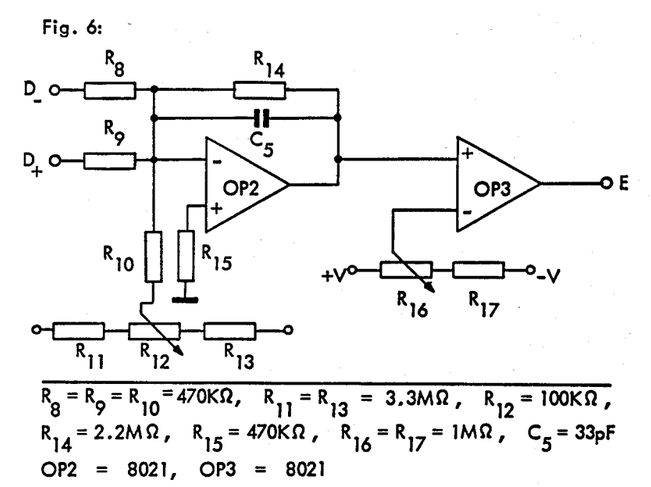
FIG. 6 is a detail of the signal conditioner, and including an adder, amplifier and comparator.

The signal conditioner 4 is illustrated in FIG. 6. It consists, as already shown in FIG. 2, of an adder, however with an offset adjustment, and a comparator postcoupled thereto. The comparator consists of an operational amplifier OP3, whose negative input is connected to a voltage divider formed by resistors $R_{16}$ and $R_{17}$. Whenever the output voltage of the amplifier OP2 exceeds the voltage level across the potentiometer $R_{16}$, the output E of the amplifier OP3 is switched from a low level to a high level. In order to damp any high-frequency voltages of a high amplitude, a capacitor $C_5$ is shunted across the feed-back resistor $R_{14}$ connected between the output and the negative input of the operational amplifier OP2, the capacitor $C_5$ limiting the amplification of the adding stage to a frequency region up to 1.5 KHz.

Figure 7:
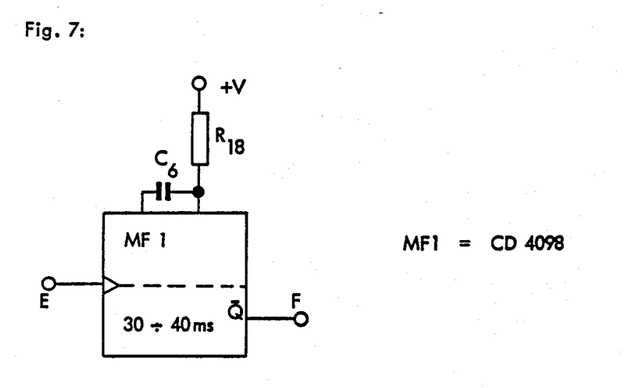
FIG. 7 is a detail of the delay circuit.

The delay circuit 5 shown in FIG. 7 does not require any detailed explanation. When a signal E is fed to the dynamic input of the multivibrator $MF_1$, the multivibrator $MF_1$ is activated, and remains for a time, advantageously selected between 30 ms and 40 ms, in the activated state. An output signal F appears on the inverted output $\overline{Q}$.

Figure 8:
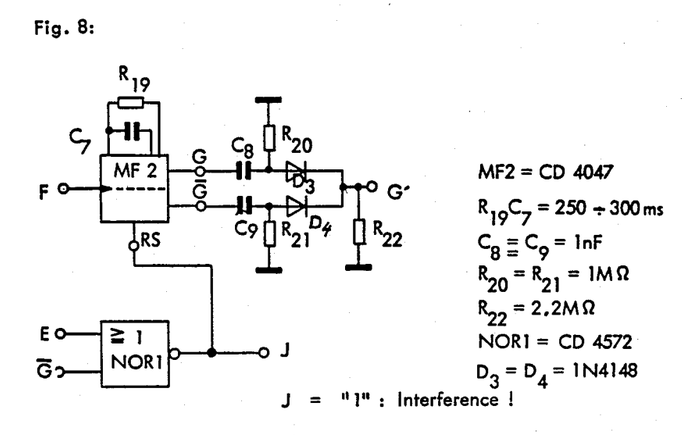
FIG. 8 is a detail of the refractory circuit.

The refractory circuit 6 shown in FIG. 8 includes additional features which have hitherto not yet been utilized in interference recognition circuits. If the monostable multivibrator $MF_2$ is activated by an input signal F, then a NOR gate NOR1 tests simultaneously for coincidence, namely whether a signal of a high or low potential appears across the output E of the signal conditioner 4 during the refractory period of the multivibrator $MF_2$, which is advantageously selected to be about 260 ms.

It will be easily understood that the reset input is always activated by a "one" signal, if any interference has caused activation of the delay circuit 5, and consequently also of the refractory circuit 6. (E and $\overline{G}$ is then "zero"). The outputs G and $\overline{G}$ are then added across the resistor $R_{22}$ through the RC circuit members $C_8$, $R_{20}$, and $C_g$, $R_{21}$, and the diodes $D_3$ and $D_4$ respectively. Consequently a positive impulse appears always on G' at the start and at the end of the refractory period, which is utilized to discharge the capacitors $C_3$ and $C_4$ in the peak-value storage stage 3 quickly through the analog switches AS1 and AS2. The refractory circuit 6, according to FIG. 8, consequently allows inputting of a refractory period of full duration (also called perceptibility pause) into the signal sequence only following a signal identified as a heart signal. In the event of any interference the refractory circuit is immediately reset, following its activation, so that there is no risk that an actual heart signal is overlooked.

Figure 9:
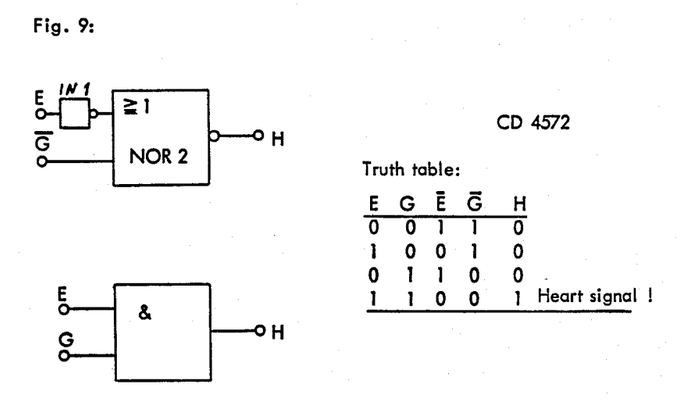
FIG. 9 is a detail of the coincidence circuit including a truth table for the circuit.

The coincidence circuit 7 according to FIG. 9 can be implemented either by an AND circuit, and wherein a signal of a high potential always appears on its output H, if both the signal E at the output of the signal conditioner 4, as well as the output signal G of the refractory circuit 6 are simultaneously signals having a high potential, or the same object can alternately be realized by a NOR gate NOR2, if the signal voltage E is inverted by an inverter IN1, and compared with the signal $\overline{G}$ of the refractory circuit 6.

I wish it to be understood that I do not desire to be limited to the exact details of construction shown and described, for obvious modifications will occur to a person skilled in the art.

Having thus described the invention, what I claim as new and desire to be secured by Letters Patent is as follows:

1. A synchronizable heart pacemaker
comprising in combination
a timing circuit for generating a stimulating impulse after an expected time interval,
differentiating means for receiving signals,
interference recognition means connected to the output of said differentiating means, and including
a testing stage for each signal, an output signal normally appearing on an output of said testing stage, said testing stage including a peak detector circuit storing a positive maximum value and a negative maximum value of each signal differentiated by an adder which further acts as an amplifier and which forms the difference of both positive and negative maximum values, and a comparator postcoupled with one input thereof to said adder and with another input thereof to a reference voltage,
a discriminator postcoupled to the testing stage, said discriminator stage generating a time interval corresponding approximately to a time duration of the QRS complex of a heart-action signal, and including checking means for checking for the presence or absence of said output signal after said time interval, and decision means for recognizing said output signal in the presence thereof within said time interval either as an interfering signal, and thereafter rendering said interfering signal ineffective, or recognizing said output signal as said heart-action signal and passing said heart-action signal to said timing circuit.

2. The heart pacemaker as claimed in claim 1, wherein said differentiating means comprises a capacitor and a resistor connected with one end thereof in series with said capacitor, and with the other end thereof to ground possessing an upper frequency limit of 1 kHz.

3. The heart pacemaker as claimed in claim 2, wherein said testing stage includes a first storage capacitor and a first diode connected in series therewith for storing said positive maximum value, and a second storage capacitor, and a second diode connected in series with said second storage capacitor for storing said negative maximum value, as well as an operational amplifier, and first and second resistors connecting said first and second capacitors, respectively, to said operational amplifier.

4. The heart pacemaker as claimed in claim 3, wherein said discriminator stage includes a monostable multivibrator having a predetermined switch-over time, said capacitors being dischargeable to a definite value within said switch-over time.

5. A synchronizable heart pacemaker for generating a current impulse after an expected time interval, said expected time interval being normally started by a heart-action signal, said heart-action signal including a QRS complex appearing within a predetermined time interval, starting with a positive-going spike, followed by a negative-going spike of a predetermined absolute magnitude and steepness followed by a positive-going spike of reduced steepness, followed in turn by a relatively broad excursion of a smaller absolute steepness than said predetermined absolute steepness, said broad excursion having a relatively low-frequency content, each of said spikes having a relatively high-frequency content, comprising in combination
a timing circuit for generating said current impulse after said expected time interval,
differentiating means for receiving signals,
interference recognition means connected to the output of said differentiating means, and including a testing stage for each signal, an output signal normally appearing on an output of said testing stage
a discriminator stage postcoupled to the testing stage, said discriminator stage including
decision means for checking the presence or absence of said output signal within said expected time interval, and heart action signal recognition means for recognizing said output signal either as an interfering signal, and thereafter rendering said interfering signal ineffective, or recognizing said output signal as said heart-action signal and passing said heart-action signal to said timing circuit in the event of the presence of said output signal within said time interval, said timing circuit being adapted to only cause generation of a current impulse passed to a stimulation electrode for stimulating the failing heart of a patient, provided no other heart-action signal occurs within said expected time interval.

6. The heart pacemaker as claimed in claim 5, wherein said discriminator stage includes a delay circuit generating a time interval corresponding to the duration of the QRS-complex, a refractory circuit postcoupled to said delay circuit generating a perceptibility pause of Q-T-duration, and a coincidence circuit postcoupled to said refractory circuit with one input thereof, and connected with another input thereof to the output of said testing stage.

7. The heart pacemaker as claimed in claim 5, wherein said delay circuit includes a first monostable multivibrator, and said refractory circuit includes a second monostable multivibrator, having a reset input enabled upon said recognition means recognizing said interference signals.

8. The heart pacemaker as claimed in claim 5, wherein said peak-value storage means includes first and second capacitors, first and second transistors connected of respective opposite polarities as emitter followers for charging said first and second capacitors, and third and fourth transistors connected as emitter followers at polarities opposite to that of said first and second transistors for feeding said stored voltages to said decision means.

9. The heart pacemaker as claimed in claim 5, wherein said peak-value storage means include first and second capacitors chargeable to respective positive and negative voltages, and further comprising first discharge means for discharging said capacitors at a slow rate, and second discharge means for discharging said capacitors at a much faster rate than said slow rate.

10. The heart pacemaker as claimed in claim 5, wherein said heart-action signal recognition means further includes steepness recognition means for recognizing said output signal as a heart-action signal only upon said negative-going spike exceeding a predetermined steepness.

11. A synchronizable heart pacemaker for generating a current impulse after an expected time interval, said expected time interval being normally started by a heart-action signal, said heart-action signal including a QRS complex appearing within a predetermined time interval, starting with an initial positive-going spike, followed by a negative-going spike of a predetermined absolute magnitude and steepness, followed by a positive-going spike of reduced steepness, followed in turn by a relatively broad excursion of a smaller absolute steepness than said predetermined absolute steepness, said broad excursion having a relatively low-frequency content, each of said spikes having a relatively high-frequency content, comprising in combination
a timing circuit for generating said current impulse after said expected time interval,
differentiating means for receiving signals, each differentiated signal having a positive peak value, and a negative peak value,
a testing stage connected to the output of said differentiating means, and including a preamplifier, peak-value storage means postcoupled to said preamplifier for storing said positive and said negative values of each signal differentiated by said differentiating means, and a signal conditioner including an adder postcoupled to said peak-value storage means, an output signal normally appearing on an output of said testing stage, said adder forming a sum from said positive and negative values, and a discriminator stage postcoupled to the testing stage, said discriminator stage including heart-action signal recognition means, including polarity-sensing means for sensing the polarity of said sum formed by said adder, and passing said output signal to said timing circuit only when said sum is negative and exceeds a predetermined absolute value, interference recognition means for recognizing any non-recurring signal having a predominantly positive rise time, and substantially any periodic pulsed or amplitude-modulated signals as interference signals, and interference suppression means for preventing said interference signals from being passed to said timing circuit, said timing circuit being adapted to only cause generation of a current impulse passed to a stimulation electrode for stimulating the failing heart of a patient, provided no other heart-action signal occurs within said expected time duration.

12. The heart pacemaker as claimed in claim 11, wherein said discriminator stage includes a delay circuit generating a time interval corresponding to the duration of the QRS-complex, a refractory circuit postcoupled to said delay circuit generating a perceptibility pause of Q-T-duration, and a coincidence circuit postcoupled to said refractory circuit with one input thereof, and connected with another input thereof to the output of said testing stage.

13. The heart pacemaker as claimed in claim 11 wherein said delay circuit includes a first monostable multivibrator, and said refractory circuit includes a second monostable multivibrator, having a reset input enabled upon said interference recognition means recognizing said interference signals.

14. The heart pacemaker as claimed in claim 11, wherein said peak-value storage means includes first and second capacitors, first and second transistors connected of respective opposite polarities as emitter followers for charging said first and second capacitors, and third and fourth transistors connected as emitter followers at polarities opposite from said first and second transistors for feeding said stored voltages to said signal conditioner.

15. The heart pacemaker as claimed in claim 11, wherein said peak-value storage means include first and second capacitors chargeable to respective positive and negative voltages, and further comprising first discharge means for discharging said capacitors at a slow rate, and second discharge means for discharging said capacitors at a much faster rate than said slow rate.

16. The heart pacemaker as claimed in claim 15, wherein said first discharge means includes a resistor.

17. The heart pacemaker as claimed in claim 15, wherein said second discharge means includes an analog switch.

18. The heart pacemaker as claimed in claim 15, wherein said second discharge means includes field effect transistors.

19. The heart pacemaker as claimed in claim 11, wherein said heart-action signal recognition means further includes steepness recognition means for recognizing said output signal as a heart-action signal only upon said negative-going spike exceeding a predetermined steepness.

20. The heart pacemaker as claimed in claim 11, wherein said discriminator stage includes a monostable multivibrator having a predetermined switch-over time, said capacitors being dischargeable to a difinite value within said switch-over time.

* * * * *